United States Patent
Hatch

(10) Patent No.: US 6,434,913 B1
(45) Date of Patent: Aug. 20, 2002

(54) SINGLE-USE SYRINGE

(76) Inventor: Thomas Hatch, 757 Rosehurst Way, Lexington, KY (US) 40515

( * ) Notice: Subject to any disclaimer, the term of this patent is extended or adjusted under 35 U.S.C. 154(b) by 88 days.

(21) Appl. No.: 09/663,234

(22) Filed: Sep. 15, 2000

(51) Int. Cl.⁷ .......................... B65B 61/00; B65B 55/04; B65B 3/04; A61M 5/00
(52) U.S. Cl. ............................ 53/410; 53/426; 53/450; 53/474; 604/110; 604/191
(58) Field of Search .......................... 53/410, 426, 428, 53/450, 452, 474; 604/110, 191, 132, 200

(56) References Cited

U.S. PATENT DOCUMENTS

| | | | |
|---|---|---|---|
| 2,469,975 A | * 5/1949 | McCloy | 53/452 |
| 2,618,263 A | 11/1952 | Lakso et al. | |
| 2,663,461 A | * 12/1953 | Brown | 53/452 |
| 2,724,383 A | 11/1955 | Lockhart | |
| 2,936,816 A | * 5/1960 | Lang | 53/452 |
| 3,385,296 A | 5/1968 | Everett | |
| 3,608,709 A | * 9/1971 | Pike | 53/474 |
| 3,696,579 A | * 10/1972 | Narusawa et al. | 53/428 |
| 3,736,933 A | 6/1973 | Szabo | |
| 3,913,734 A | 10/1975 | Siegel | |
| 3,946,732 A | 3/1976 | Hurscham | |
| 3,964,604 A | 6/1976 | Prenntzell | |
| 4,022,206 A | 5/1977 | Hilleman et al. | |
| 4,035,924 A | 7/1977 | Faure | |
| 4,176,153 A | 11/1979 | Weiler et al. | |
| 4,239,726 A | 12/1980 | Weiler et al. | |
| 4,342,184 A | * 8/1982 | Van Eck et al. | 53/452 |
| 4,425,090 A | 1/1984 | Hansen | |
| 4,484,920 A | 11/1984 | Kaufman et al. | |
| 4,501,719 A | 2/1985 | Williams | |
| 4,602,910 A | 7/1986 | Larkin | |
| 4,613,531 A | 9/1986 | Gokcen et al. | |
| 4,645,486 A | 2/1987 | Beal et al. | |
| 4,692,151 A | * 9/1987 | Blackman | 604/132 |
| 4,709,534 A | * 12/1987 | Sengewald | 53/452 |
| 4,926,915 A | * 5/1990 | Deussen et al. | 604/200 |
| 4,953,299 A | 9/1990 | Gimeno et al. | |
| 5,169,389 A | * 12/1992 | Kriesel | 604/132 |
| 5,192,272 A | * 3/1993 | Faure | 604/132 |
| 5,207,320 A | * 5/1993 | Allen | 53/474 |
| 5,309,649 A | 5/1994 | Bergmann et al. | |
| 5,558,874 A | 9/1996 | Haber et al. | |
| 5,689,898 A | 11/1997 | Renzi | |
| 6,019,752 A | 2/2000 | Sunago et al. | |
| 6,071,005 A | 6/2000 | Ekambaram et al. | |
| 6,071,270 A | 6/2000 | Fowles et al. | |

FOREIGN PATENT DOCUMENTS

| | | |
|---|---|---|
| GB | 2154882 | 9/1985 |
| WO | WO 90/01960 | 3/1990 |

* cited by examiner

*Primary Examiner*—Stephen F. Gerrity
*Assistant Examiner*—Louis Huynh
(74) *Attorney, Agent, or Firm*—Kevin M. Farrell

(57) ABSTRACT

Disclosed is a method for producing a single use syringe. A tube, open at both ends, is provided. A plurality of needles fixed to a tether in spaced-apart relation are also provided, each needle having a proximal and a distal end. The tether and plurality of fixed needles are then deployed by introducing a first end of the tether into a first end of the tube and translating the first end of the tether to the second end of the tube thereby deploying the needles in spaced-apart relation along the length of the tube. A predetermined fluid volume is introduced into the tube and the tube is sealed at spaced-apart intervals to create a web comprising individual single use syringes, each single use syringe comprising a single needle and a fluid volume.

14 Claims, 1 Drawing Sheet

SINGLE-USE SYRINGE

BACKGROUND OF THE INVENTION

The storage and dispensing of fluids, and more particularly sterile fluids used in medical applications requiring use of a needle, is plagued by a host of difficulties which detract from the optimal use of such sterile fluids. For example, in cost-sensitive applications, multi-dose vials provide an economical means of packaging medical fluids but also increase the likelihood of contamination of the remaining contents when multiple needles are used to penetrate the sterile environment of the vial. This is an even greater problem in animal health applications where the same needle is often used to inject a medical fluid such as a vaccine into multiple animals. Re-entry of a contaminated needle into the multi-dose storage container may lead not only to a loss of sterility but to severe contamination of the remaining contents with infectious disease causing organisms. Such contamination may require the disposal of the remaining non-sterile medical fluid if not used immediately, or worse, the transmission of infectious disease organisms between animals.

When conventional syringes are used to draw fluids such as vaccines from multi-dose vials, considerable time and effort can be lost in the process, particularly in animal applications. The user must go to a cold storage area, locate a vial containing the desired fluid, transport the vial to the location where the fluid is to be administered, penetrate the sterile barrier of the vial with a needle, withdraw a single dose of fluid, and administer the dose to the animal. In many instances the vial is stored in a refrigerator at some distance from where the fluid is to be administered, particularly when the animal being treated is located in the field. After use, the vial containing the remaining fluid must be returned immediately to the refrigerator to maintain product quality. The time cost of maintaining cold chain conditions on the medical fluid can be a major inconvenience to the user and can result in variable observation of handling instructions on the product label. For the reasons discussed above, a cost-effective, preloaded, single-use syringe would represent a major advance in the art.

SUMMARY OF THE INVENTION

Figure 1:
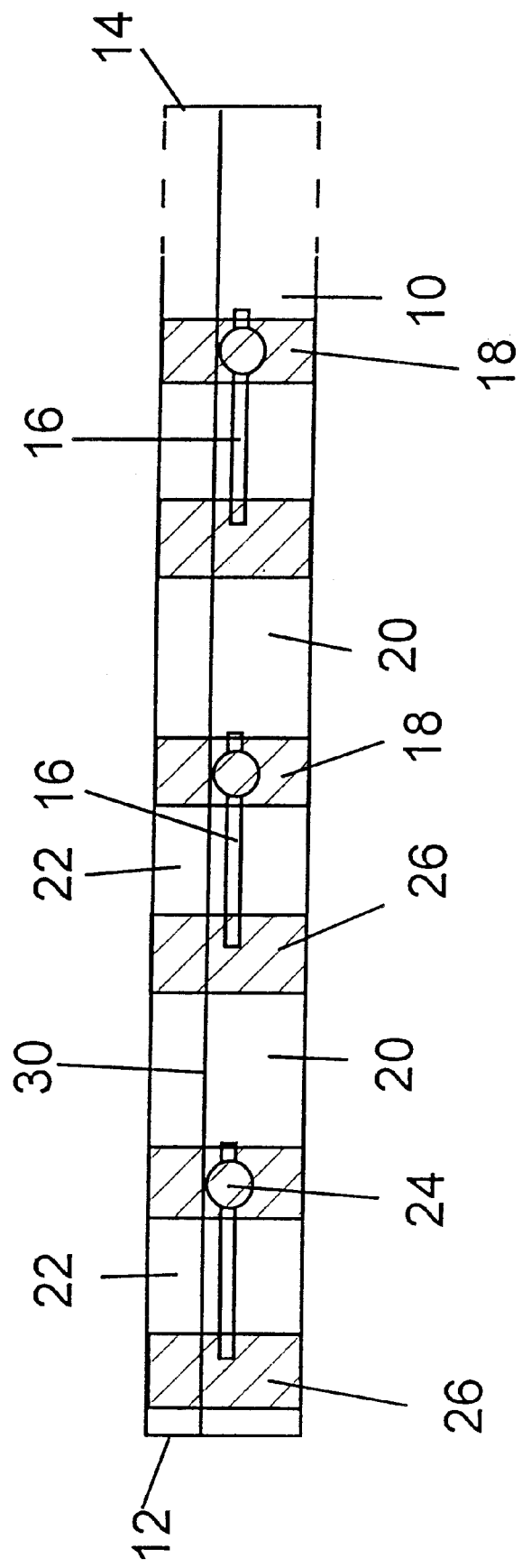
FIG. 1 is a top view of a linked series of single-use syringes produced according to the method of the present invention.

The present invention relates to a method for producing a single use syringe. A tube, open at both ends, is provided. A plurality of needles fixed to a tether in spaced-apart relation are also provided, each needle having a proximal and a distal end. The tether and plurality of fixed needles are then deployed by introducing a first end of the tether into a first end of the tube and translating the first end of the tether to the second end of the tube thereby deploying the needles in spaced-apart relation along the length of the tube. A predetermined fluid volume is introduced into the tube and the tube is sealed at spaced-apart intervals to create a web comprising individual single use syringes, each single use syringe comprising a single needle and a fluid volume.

DESCRIPTION OF PREFERRED EMBODIMENTS

The present invention relates to a method for producing a single use syringe. The method represents an extremely cost-effective means for producing pre-loaded single-use syringes for medical, veterinary and other commercial applications. Generally speaking, embodiments of the present invention include methods in which a plurality of needles are deployed along the length of a flexible tube. The tube is then filled with a fluid and sealed at spaced-apart intervals to form individual single-use syringes.

Referring to FIG. 1, a flexible tube 10 is shown. Tube 10 has a first end 12 and a second end 14. In preferred embodiments, the tube 10 is produced from a flexible heat-sealable material. Such materials include, for example, thermoplastics (e.g., fluorocarbon and vinyl-chloride materials), foils and polyfoils. Tubing which retains a substantially round shape even in the absence of any contained fluid volume is preferred. Dupont's Tygon (registered trademark) is an example of a commercially available tubing useful in connection with the method of the present invention.

A plurality of bore-containing needles 16 are provided having a diameter suitable for the application of interest. For example, if the single use syringes are to be used for intravenous injection of fluids into an animal, 18 gauge needles would be appropriate. An important step in the method of the present invention is the step in which a plurality of needles are deployed in spaced-apart relation along the length of the tube. Practically speaking, the upper limit for the number of needles deployed in a single production run along a single length of tubing is in the thousands. It is likely, however, that a more common production run would result in the deployment of hundreds of needles along the length of the tubing.

A variety of methods are useful for the deployment of the plurality of needles along the length of tubing. For example, needles 16 may be attached in spaced-apart relation to a tether 30. The tether 30 is preferably attached at the proximal end of needle 16. The distance between the spaced apart needles on the tether is determined primarily by the desired volume which the individual single-use syringes are designed to deliver. This determination is a matter of routine experimentation to one skilled in the art. As will be discussed below, heat sealing is a preferred method for sealing thereby introducing alternating fluid volume regions and needle sheath regions. In light of the fact that heat sealing is a preferred method for sealing, it is also preferable that the tether be produced from a heat-sealable material (e.g., thermoplastic, foil or polyfoil).

The tether, with needles attached in spaced-apart relation, is then used to deploy the needles. More specifically, a first end of the tether is introduced into a first end of the tube and translated to the second end of the tube thereby deploying the needles in spaced-apart relation along the length of the tube. The contents are then rendered pyrogen free by conventional techniques.

A predetermined fluid volume is then introduced into the tube. Any type of fluid may be introduced into the tube. For many medical applications, the tube and needles are sterilized prior to introduction of the fluid of interest. A variety of sterilization methods may be employed including, for example, exposure to high temperature, irradiation, and sterilizing fluids or gases. The amount of fluid to be introduced is empirically optimized to reduce waste. For example, one-half of the volume of the tube is a good starting point for empirical determination.

Following fluid introduction, the tube is sealed (e.g., by heat-sealing) to form individual single-use syringes. The web is sealed at spaced-apart intervals to create a web comprising individual single-use syringes, each single-use syringe comprising a single bore-containing needle in liquid communication with a contained fluid volume. Such seals are conveniently introduced by pressing a heated element onto the heat-sealable tube at spaced-apart intervals. The width of the heated element (and therefore the width of the seal) is selected to ensure good fluid-tight sealing and needle stabilization. Consideration of subsequent separation and use of individual syringes is also considered when designing sealing patterns.

In preferred embodiments, a plurality of seals are introduced to form each single use syringe, the plurality of seals forming two or more alternating regions in the sealed tube, including a fluid volume region and a needle sheath region. One of skill in the art could design a large number of effective sealing patterns, all of which are within the scope of the present invention. For example, referring again to FIG. 1, proximal needle-end seals 18 are introduced to form one end of the fluid volume region 20 and one end of the needle sheath region 22. These seals are positioned such that they do not occlude the needle bore and they hold the needle firmly in place.

FIG. 1 also shows a second seal which will be referred to herein as a fluid volume seal 26. Fluid volume seal 26 together with two adjacent needle-end seals 18, defines needle sheath region 22 and fluid volume region 20. In the embodiment shown in FIG. 1, fluid volume seal 26 overlaps the distal end of needle 16, thereby stabilizing needle 16 within the needle sheath region 22 thereby reducing the possibility that the tube 10 could be inadvertently punctured by a splaying movement of the distal needle end. It is not necessary that the fluid volume seal 26 overlap the distal end of needle 16. It should be noted that additional seals could be provided for added security. For example, a needle stabilization seal could be introduced in the needle sheath region 22 between seals 18 and 26 for added security.

In preferred embodiments, an attachment element 24 is provided. The needle attachment element serves multiple functions. The needle attachment element 24 can serve as an anchorage for tether 30. In addition, if deformable and heat-sealable, the attachment element 24 can participate as an element in the heat sealing process thereby assuring a tight seal around needle 16.

In preferred embodiments, the needle sheath regions 22 do not contain a substantial fluid volume relative to the fluid volume containing region. During the sealing process, for example, a roller could function to expel much of the fluid from the needle sheath region 22 prior to the introduction of the seal which closes and defines the needle sheath region. This step would serve to minimize the fluid waste associated with production.

Upon completion of the sealing process, the resulting sealed tube comprising a linked series of individual single-use syringes can be rolled for shipping. Alternatively, the single-use syringes can be separated from one another (e.g., by cutting) and boxed individually for shipment. As an alternative to cutting, perforations can be introduced during the manufacturing process to facilitate subsequent separation of individual single-use syringes from the linked series, and/or to facilitate removal of the needle sheath region prior to use.

What is claimed is:

1. A method for producing a single use syringe, comprising:

a) providing a tube open at both ends;

b) providing a plurality of needles fixed to a tether in spaced-apart relation, each needle having a proximal and a distal end;

c) deploying the tether and plurality of fixed needles by introducing a first end of the tether into a first end of the tube of step a) and translating the first end of the tether to the second end of the tube thereby deploying the needles in spaced-apart relation along the length of the tube;

d) introducing a predetermined fluid volume into the tube; and e) sealing the tube at spaced-apart intervals to create a web comprising individual single use syringes, each single use syringe comprising a single needle and a fluid volume.

2. The method of claim 1 wherein a plurality of seals are introduced during step e) to form each single use syringe, the plurality of seals forming two alternating regions in the sealed tube, a fluid volume region and a needle sheath region.

3. The method of claim 2 wherein the needle sheath regions do not contain a substantial fluid volume.

4. The method of claim 2 wherein perforations are introduced to facilitate separation of individual single use syringes and/or removal of the needle sheath region from individual single use syringes.

5. The method of claim 1 wherein each needle has an attachment element secured to the proximal end of the needle.

6. The method of claim 1 wherein the tube is produced from a heat-sealable material.

7. The method of claim 6 wherein the heat-sealable material is a thermoplastic, foil or polyfoil material.

8. The method of claim 7 wherein sterilization is accomplished by a method selected from the group consisting of exposure to high temperature, irradiation, and sterilizing fluids or gases.

9. The method of claim 1 wherein the needle has a blunt point.

10. The method of claim 1 wherein the tether is produced from a heat-sealable material.

11. The method of claim 10 wherein the heat-sealable material is a thermoplastic, foil or polyfoil material.

12. The method of claim 1 wherein the interior of the tube and its contents are sterilized prior to filling with fluid.

13. The method of claim 1 wherein the volume of the fluid introduced into the tube is approximately half the total volume of the tube.

14. The method of claim 1 wherein individual single use syringes are separated from one another by cutting.

* * * * *